United States Patent [19]
Punto et al.

[11] Patent Number: 5,662,890
[45] Date of Patent: Sep. 2, 1997

[54] SELF-TANNING COSMETIC COMPOSITIONS AND METHODS OF USING THE SAME

[75] Inventors: Louis L. Punto, Northport, N.Y.; Jules R. Zecchino, Closter, N.J.; Peter J. Lentini, Glen Oaks, N.Y.

[73] Assignee: Estee Lauder, Inc., New York, N.Y.

[21] Appl. No.: 320,772

[22] Filed: Oct. 11, 1994

Related U.S. Application Data

[63] Continuation of Ser. No. 980,001, Nov. 23, 1992, abandoned.

[51] Int. Cl.⁶ .................................................. A61K 7/42
[52] U.S. Cl. .................... 424/59; 424/60; 514/938; 514/946; 514/947
[58] Field of Search .................. 424/59, 60; 514/938, 514/946, 947

[56] References Cited

U.S. PATENT DOCUMENTS

| | | | |
|---|---|---|---|
| 2,949,403 | 8/1960 | Andreadis et al. | 167/90 |
| 3,177,120 | 4/1965 | Black et al. | 167/90 |
| 3,184,388 | 5/1965 | Kalopissis | 424/60 X |
| 4,145,413 | 3/1979 | Usdin et al. | 424/63 |
| 4,383,986 | 5/1983 | Dubash et al. | 424/25 |
| 4,434,154 | 2/1984 | McShane | 424/60 |
| 4,708,865 | 11/1987 | Turner | 424/59 |
| 4,711,904 | 12/1987 | Luzzi et al. | 514/464 |
| 4,746,509 | 5/1988 | Haggiage et al. | 424/449 |
| 5,059,426 | 10/1991 | Chiang et al. | 424/449 |
| 5,071,657 | 12/1991 | Oloff et al. | 424/486 |
| 5,431,902 | 7/1995 | Cuine et al. | 424/45 |

OTHER PUBLICATIONS

Clement et al, 1989, Chem. Abs., vol. 113 (16); 138317S.
Cooper and Patel, 1990, "Practical Considerations for Topical Drug Formulations With and Without Enhancers", *Topical Drug Delivery Formulations* (Marcel Dekker, Inc., New York) pp. 1–12.

*Primary Examiner*—Shelley A. Dodson
*Attorney, Agent, or Firm*—Pennie & Edmonds LLP

[57] ABSTRACT

The present invention relates to novel cosmetic preparations for artificially tanning the skin. These novel cosmetics are applied to the skin in a sprayable mist application. These cosmetics are oil and alcohol free and are quick drying. Further, these cosmetic preparations provide an even, deeper and long lasting artificial tan.

14 Claims, 8 Drawing Sheets

SELF-TANNING COSMETIC COMPOSITIONS AND METHODS OF USING THE SAME

This is a continuation of application Ser. No. 07/980,001, filed Nov. 23, 1992, now abandoned, which is incorporated by reference herein in its entirety.

1. FIELD OF THE INVENTION

This invention relates to cosmetic compositions for providing an artificial tan on skin and a method of using the same. More specifically, the invention relates to a cosmetic composition useful as a self-tanning agent when topically applied to the skin which has excellent evenness, depth and longevity of the artificial tan while having excellent drying properties.

2. BACKGROUND OF THE INVENTION

U.S. Pat. No. 2,949,403 discloses compositions of and methods of using dihydroxyacetone as a tanning agent for the human epidermis. It has been reported that dihydroxyacetone reacts with skin proteins and amino acids to elicit its skin coloring effect. Since the 1960's, several compositions using dihydroxyacetone as an active ingredient have been reported. These compositions include a topical solution containing dihydroxyacetone and various dyes such as catch powder, dogwood powder and walnut powder (the dyes are employed to offset the undesirable orange cast or hue which results from the use of dihydroxyacetone on fair skinned humans, see U.S. Pat. No. 4,708,865); and compositions containing dihydroxyacetone and sunscreen compounds such as octyl dimethyl PABA (e.g., U.S. Pat. Nos. 4,434,154 and 3,177,120).

Further, dihydroxyacetone has been formulated into oil-in-water emulsions, into preparations containing up to 50% alcohol which tends to dry the skin, and into "creamy bases" such as are found in hand and face lotions and creams. Moreover, Andreadis et al. in U.S. Pat. No. 2,949,403 state that dihydroxyacetone may be carried or suspended in various cosmetic bases suitable for external application directly to the skin. Andreadis et al. state that for external applications such bases may take the form of liquid or cream lotions, ointments, dusting powders and the like.

To date, all the vehicles used for applying dihydroxyacetone to the skin have been creams and lotions of emulsions containing either oils or alcohols. In a cream or lotion form, dihydroxyacetone must diffuse from the base into the skin. Therefore, the common excipients used in these forms, i.e., emulsifiers, oils, waxes, etc., trap a portion of the dihydroxyacetone in the surface film which is on top of the skin thereby making it unavailable for reaction with skin proteins or amino acids. This results in loss of depth and longevity of the artificial tan.

It is an object of the present invention to provide a more convenient method of applying dihydroxyacetone to the skin. Another object of the present invention is to provide a quick drying self-tanning composition.

It is also an object of the present invention to provide an alcohol-free, oil-free self-tanning composition containing dihydroxyacetone.

It is a further object of the present invention to provide a water-based spray-on self-tanning composition.

Another object of the present invention is to provide a cosmetic self-tanning composition which imparts a deeper, longer lasting tan than the prior art compositions. It is an object of the present invention to provide a composition for artificially tanning human skin which provides a coloring that closely resembles natural tan coloring.

It is yet another object of the present invention to provide an improved skin tanning cosmetic which may be delivered in an atomized droplet form for deeper skin penetration and overall superior tanning effects.

3. SUMMARY OF THE INVENTION

It has been discovered that the novel aqueous based self-tanning compositions of the present invention provide a deeper, longer lasting artificial tan than known self-tanning compositions. It has further been discovered that the artificial tan achieved with the present invention is more similar in color to a natural tan than any known self-tanning compositions. The present invention encompasses a self-tanning (artificial skin coloring) composition useful as a cosmetic for the skin which comprises an aqueous dermatologic base, dihydroxyacetone ("DHA") and optionally, aqueous penetration enhancers including but not limited to dimethylisosorbide and diethylene glycol monoethylether.

The compositions of the present invention are suitable for application to the skin in the form of a mist or spray which is possible through the use of an aerosol or spray-on applicator i.e., the compositions are applied to the skin in an atomized droplet form. In the present aqueous base system, the dihydroxyacetone has improved absorption into the skin yielding a deeper and more even penetration into the skin, which provides a deeper, more even longer lasting artificial tan. Therefore, the cosmetic compositions of the present invention are an improvement over currently available skin tanning systems. Moreover, the cosmetic compositions of the present invention are more convenient to use because they are quick drying.

The present invention further encompasses a method of tanning the skin (i.e., of imparting an artificial tan to the skin) which comprises topically applying to the skin an amount of the novel self-tanning compositions, said amount being sufficient to impart an artificial tan to the skin wherein said tan is deeper, more even and longer lasting than the tan achieved by currently available or prior systems.

4. BRIEF DESCRIPTION OF THE FIGURES

The accompanying figures, which are incorporated in and constitute a part of the specification, illustrate embodiments of the invention and, together with the description, serve to explain the principles of the invention.

Figure 6:
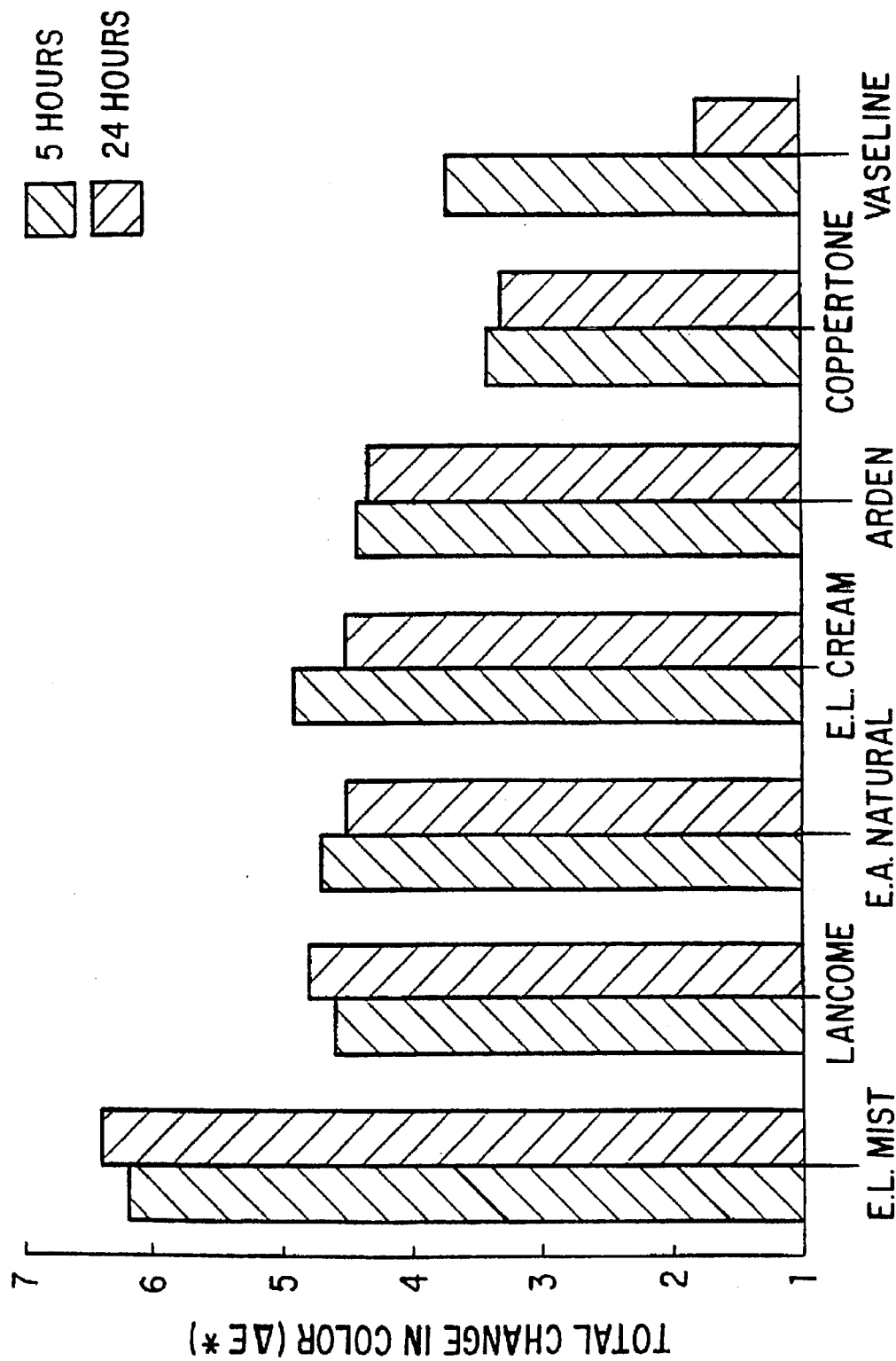

FIG. 6 is a bar graph illustrating the total color change achieved with several self-tan products vs. E.L. Selftan Mist, 5 and 24 hours after application.

Figure 7:
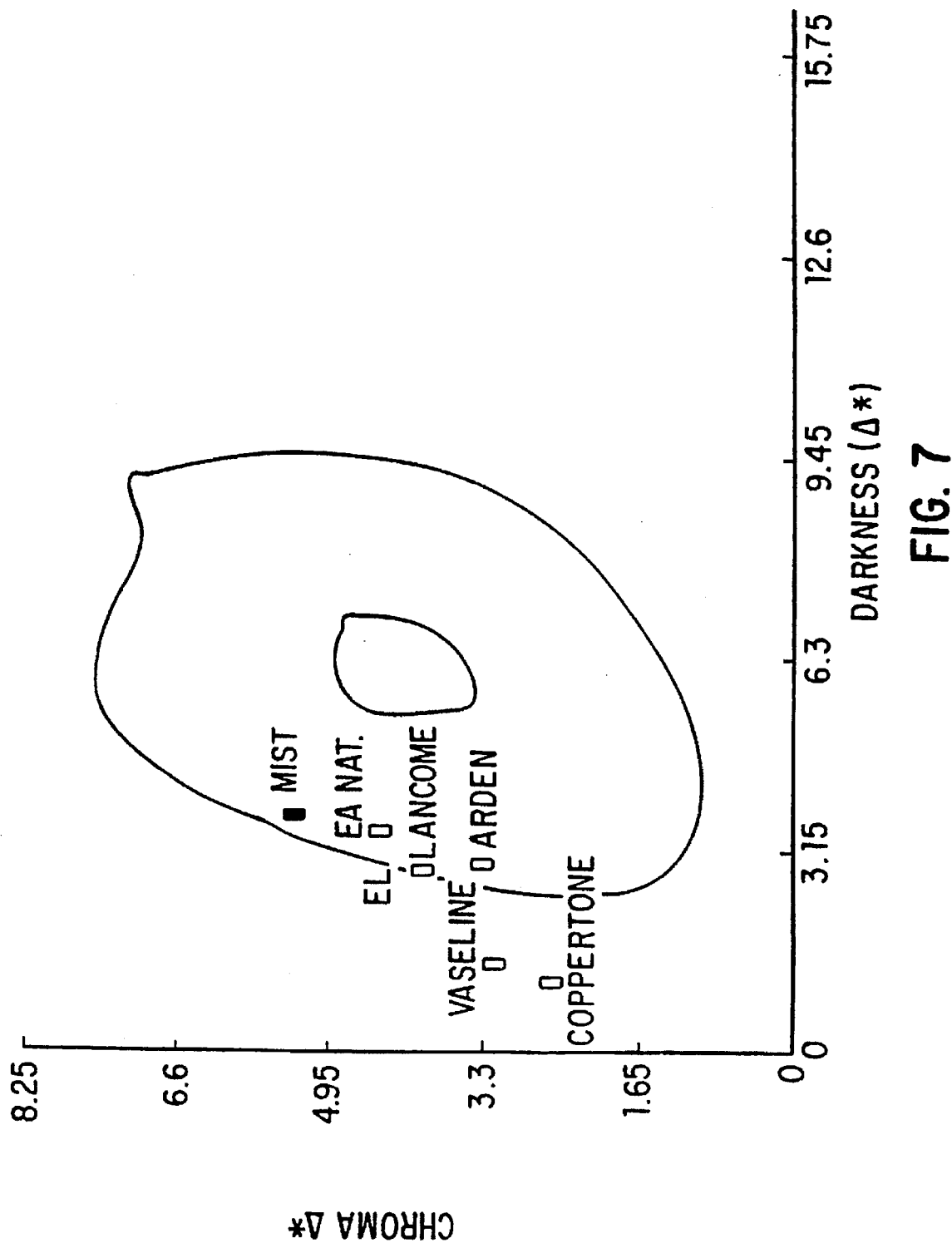
Figure 8:
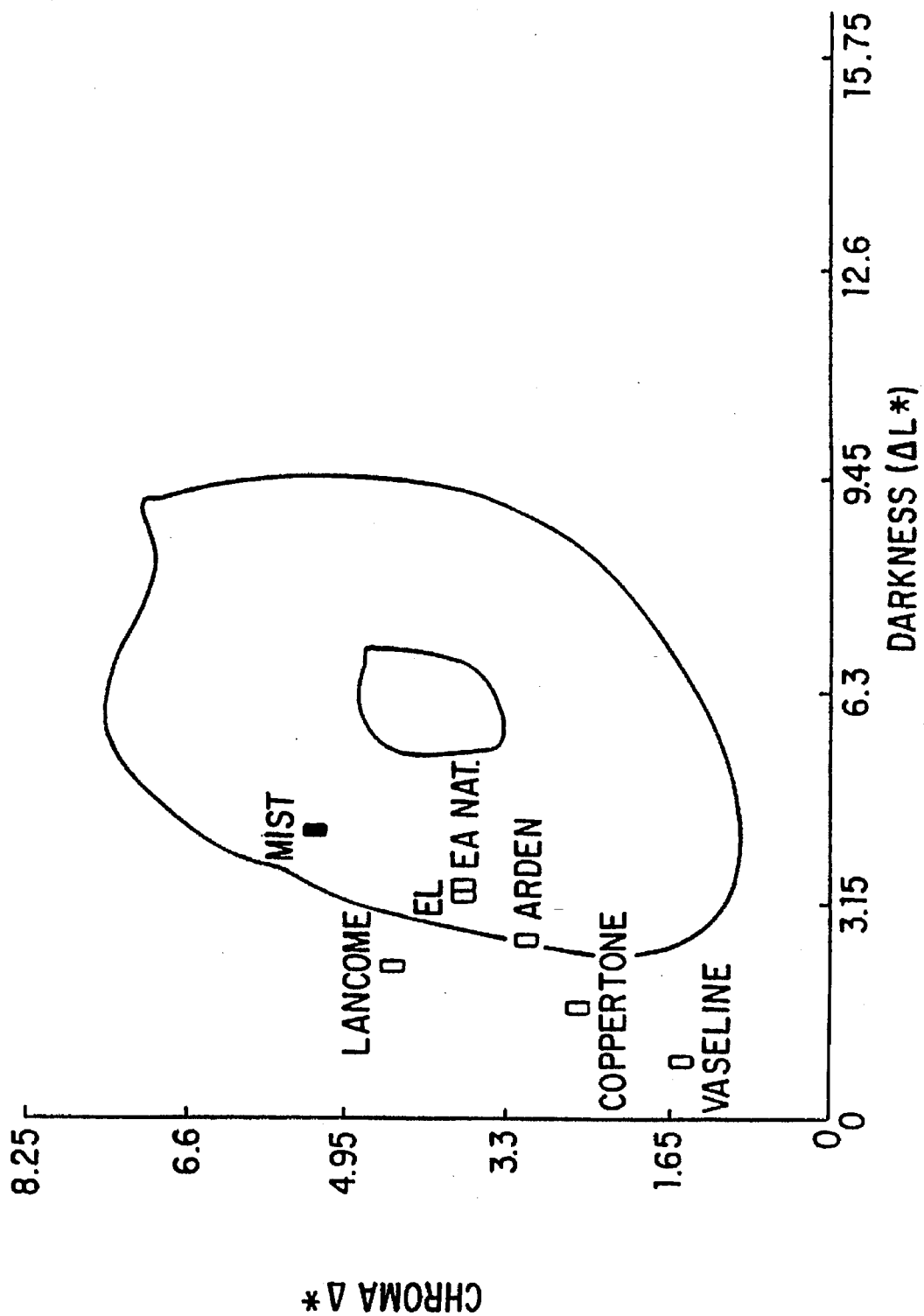

FIGS. 7 and 8 are plots illustrating the difference in color of the artificial tan, in particular, the relation to that of a natural tan, for several selftan products including E.L. Selftan Mist. The plot represents the "natural universe of tan".

5. DETAILED DESCRIPTION OF THE INVENTION

The present invention is a self-action tanning composition useful for imparting an artificial tan to skin by topical application in the form of a mist or spray. The present novel compositions are formulated into an aqueous base system comprising dihydroxyacetone ("DHA") as the active ingredient. Surprisingly, the aqueous base system allows for a greater absorption of DHA by the skin primarily because of the low level of excipients which can trap, portions of the DHA in the surface film making it unavailable for reaction with skin proteins and/or amino acids.

The aqueous base system of the present invention provides an additional improvement over currently available creams and emulsions because the system allows for the application of the product in the form of a mist or spray. The mist type application delivers the product in an atomized droplet form which further improves penetration and absorption of the DHA into the skin. The greater absorption of DHA achieved by the present invention allows for a deeper and longer lasting tan than that achieved by the currently available emulsion or cream systems. In addition, the mist type application of the present invention provides for a quicker drying composition. See Examples and Tables, infra.

Furthermore, in an aqueous base, DHA can have an even greater absorption with the use of aqueous soluble penetration enhancers. The use of aqueous soluble penetration enhancers in conjunction with the present invention provides yet another benefit since the penetration enhancers assist with the penetration of DHA into the skin. This invention constitutes the first use, known to the inventors, of penetration enhancers in this type of product, i.e., a self-action tanning product. Moreover, because the penetration enhancers can be used at levels not normally used in emulsion systems an even greater effect can be achieved. Generally, at high levels penetration enhancers are difficult to emulsify and destabilize the emulsion in which they are present, therefore high levels are not used in emulsion systems. The use of such penetration enhancers provides yet a higher DHA penetration than that achieved by the emulsion systems.

Suitable penetration enhancers for use in the present invention are known to those skilled in the art and can be found in the CTFA International Cosmetic Ingredient Dictionary 4th Edition, The Cosmetics, Toiletries and Fragrance Association, Washington, D.C., 1991. These penetration enhancers must be able to solubilize DHA. The preferred penetration enhancers include but are not limited to dimethyl isosorbide (Ariasolve® DMI, ICI Americas) and diethylene glycol monoethyl ether (Transcutol®, Gatte fosse).

Moreover, as discussed above, because the present invention allows the compositions to be delivered in an atomized droplet form, the DHA also penetrates deeper and develops better than conventional forms. While not being limited to any theory, it is believed that as the composition is broken up into a mist, certain volatile components flash off; as the product reaches the skin, in a very small droplet size compared to other delivery systems (e.g., creams or emulsions), a more concentrated DHA solution is available to penetrate and bind to the skin. Optionally, with the help of the non-volatile penetration enhancers and this smaller droplet size, a more concentrated DHA solution penetrates farther down into the skin giving a deeper, longer lasting tan.

The present invention encompasses an aqueous base self-tanning composition which comprises about 25 to about 95% water by weight percent of the total composition, preferably purified or deionized water; about 2.5 to about 10% by weight of dihydroxyacetone; and optionally about 5 to about 75% by weight of one or more penetration enhancers including but not limited to dimethyl isosorbide and diethyl glycol mono ethyl ether.

Various optional ingredients may be included in the compositions of the present invention, these include but are not limited to perfumes, preservatives, emollients, antiseptics, pigments, dyes, humectants, propellants, as well as other classes of materials whose presence may be cosmetically, medicinally or otherwise desirable. Common examples can be found in the CTFA International Cosmetic Ingredient Dictionary 4th Edition, The Cosmetic, Toiletry, and Fragrance Association, Inc., Washington, D.C., 1991. Common examples of such ingredients are provided below by way of example and not limitation.

Optional ingredients include polyoxyethylene ethers such as PPG-12-buteth-16 (UCON 50 HB 660), PPG-3-buteth 5, PPG-5-buteth 7, PPG-7-buteth 10, PPG-9-buteth 12, PPG-12-buteth 16, PPG-15-buteth 20, PPG-20-buteth 30, PPG-28-buteth 35, PPG-33-buteth 45, PEG-4, PEG-6, PEG-8, PEG-10, PEG-12, PEG-32, or suitable ingredients which provide emolliency; hydrolyzed wheat protein/wheat oligosaccharides such as Cropeptide W®, hydrolyzed corn protein, hydrolyzed corn starch, hydrolyzed wheat gluten, hydrolyzed yeast protein, hydrolyzed vegetable protein, hydrolyzed soy protein, hydrolyzed rice protein, hydrolyzed potato protein, which are suitable for moisturization; polyethylene glycol esters such as PEG-14 Laurate, PEG-15 Laurate, PEG-20 Laurate, PEG-32 Laurate, PEG-75 Laurate, PEG-150 Laurate or other surfactants which are used for fragrance solubilization; glycereth-7-triacetate (Dermol GL-7A, Alzo), glycerin, glycereth 5 lactate, glycereth 7 diisonanoate which are used for moisturization, emolliency and to help solubilize fragrance; PEG-40 Castor Oil (Surfactol 365, CasChem), PEG 45 castor oil, PEG 50 castor oil, PEG 60 castor oil, PEG 100 castor oil which are surfactants to help solubilize fragrance and also provide emolliency and moisturization; preservatives such as methyldibromo-glutaronitrile/phenoxyethanol/polyquaternium-7 (Euxyl K-400, Calgon) methyl paraben, imidazolidinyl urea benzalkonium chloride, diazolidinyl urea, benzethonium chloride, sodium benzoate and sorbic acid; sunscreens such as octyldimethyl PABA, benzophenone-4, DEA-methoxycinnamate, 2-phenylbenzimidazole-5-sulphonic acid and TEA salicylate; and finally fragrances.

The aqueous base self-tanning compositions of the present invention do not contain alcohols or oils, as is typical of currently available systems. As used herein, the term "alcohols" refers to common solvents known to those skilled in the cosmetic art; these include but are not limited to ethanol and isopropyl alcohol. The term "alcohols" as used herein is not meant to encompass polyols, i.e., compounds with more than one hydroxyl group. Similarly, as used herein, "oil free" means that the cosmetic composition does not contain ingredients such as mineral oil, rice oil, almond oil, and jojoba oil and other oils commonly used by those skilled in the art.

As used herein the terms "tanning of the skin", "coloring of the skin" or "artificially tanning the skin" mean that a simulated natural tan effect is produced on the skin, particularly the epidermis.

As used herein the term "atomized droplet form" means that the composition is not delivered as cream or emulsion type composition but in the form of particles achieved by spray applicators, aerosol applicators and other such applicators known to those skilled in the art.

The compositions of the present invention are prepared by the following preferred procedure which is performed at room temperature and pressure. Other procedures known to those skilled in the art may also be used. The procedure refers to the ingredients found in E.L. Self-Action Tanning Mist.

E.L. Self-action Tanning Mist

| Ingredient | Sequence | Percent Weight |
| --- | --- | --- |
| Deionized Water | 1 | 63.1 |
| Dihydroxyacetone | 2 | 5.0 |
| 1,3 butylene glycol | 3 | 3.0 |
| UCON 50 HB 660 | 3 | 0.5 |
| Cropeptide W | 3 | 0.2 |
| Arasolve DMI | 3 | 10.0 |
| Protomate 600-ML | 3 | 1.5 |
| Euxyl K-400 | 4 | 0.2 |
| Transcutol | 4 | 10.0 |
| Dermol GL-7A | 4 | 5.0 |
| Surfactol 365 | 5 | 1.0 |
| Fragrance | 6 | 0.5 |

1. Add the deionized water (Sequence 1) to the main kettle equipped with a Lightnin mixer and begin moderate agitation.
2. Sprinkle dihydroxyacetone (Sequence 2) into the deionized water (Sequence 1) and mix until dissolved.
3. Add Sequence 3 one at a time to the main kettle and mix until dissolved.
4. In a separate vessel, add the Dermol GL-7A of Sequence 4 and begin moderate Lightnin mixer agitation. Add the fragrance and mix until dispersed. Add the surfactol 365 and mix for 5 minutes. Add Sequence 4 to the main kettle.
5. Add Sequence 5.
6. Add Sequence 6 and mix for 10 minutes.
7. Stop mixing and pump product through a 10 m filter into poly-lined drums.

Additional spray-on self tanning compositions are prepared as described above. These have the following formulas:

| Ingredient | Percent Weight |
| --- | --- |
| Deionized water | 53.35 |
| Methyl paraben | 0.10 |
| Glycerin | 3.00 |
| DHA | 5.00 |
| Arlasolve DMI | 20.00 |
| Procetyl AWS | 3.00 |
| Fragrance | 0.25 |
| Transcutol | 15.00 |
| Sorbic acid | 0.10 |
| Hydrolyzed vegetable protein | 0.20 |

| Ingredient | Percent Weight |
| --- | --- |
| Deionized water | 77.25 |
| Eusolex 232 | 1.00 |
| Butylene glycol | 3.00 |
| TEA | 0.70 |
| DHA | 5.00 |
| UCON 50 HB 660 | 1.00 |
| Arlasolve DMI | 5.00 |
| Transcutol | 5.00 |
| Cropeptide W | 0.20 |
| Surfactol 365 | 1.50 |
| Fragrance | 0.25 |
| Euxyl K-400 | 0.10 |

The compositions of the present invention are applied to the skin using a spray pump applicator, spray bladder packages and aerosols powered by compressed gas. The compositions are applied evenly to the skin and should be applied to dry skin after exfoliating. Color will develop several hours after the application and Will last for about 4 to about 8 days.

The invention is further defined by reference to the following examples which are set forth by way of example and not limitation.

EXAMPLES 6.1 Example 1

DEPTH AND EVENNESS OF SELF-ACTION TANNING COMPOSITIONS

E.L. SELF-ACTION TANNING CREAM VS. MIST

This example compares the depth and evenness of the tan achieved with Self-Action Tanning Mist (B) and Self-Action Tanning Cream (A). The skin coloration with the Selftan Mist (B) was deeper than the cream as observed after 20 Scotch Tape Strippings. The Selftan Mist also gives more even tones as observed by the low standard of deviation of the color replicates.

This experiment was designed to compare the depth and evenness of self-action tanning effect of E.L. Self-action Tanning Cream and Mist on increasing skin color. The following products were tested:

A. E.L. Self-action Tanning Cream

| Ingredient | Weight Percent |
| --- | --- |
| Tween 85 | 2.0 |
| Arlacel 165 | 2.5 |
| Glyceryl Monostearate (pure) | 1.0 |
| Polawax Regular/Lipowax P | 4.75 |
| Ceraphyl 50 | 2.4 |
| Crodafos SG | 1.2 |
| Lexol GT-865/Liponate GC | 9.5 |
| Bernel Ester TOC | 4.0 |
| Silicone Fluid 556 | 4.5 |
| Wax 580A | 0.3 |
| Propyl Paraben | 0.1 |
| Butyl Paraben | 0.05 |
| Dehydroacetic Acid | 0.1 |
| Allantoin | 0.1 |
| Veegum HV (4% Disp.) | 32.0 |
| Deionized Water | 15.03 |
| Sorbic Acid (Surbistat SOR) | 0.05 |
| Methyl Paraben USP | 0.3 |

-continued

| Ingredient | Weight Percent |
| --- | --- |
| Ethylparaben | 0.07 |
| Propyl Paraben | 0.05 |
| Sequestrene NA3 | 0.1 |
| Phosphoric Acid (50% Aq. Soln) | 0.2 |
| Cyanamer N-300 LMW (1% Aq. Soln) | 2.6 |
| Fragrance 561/1 | 0.75 |
| Deionized Water | 5.0 |
| Propylene Glycol USP | 5.0 |
| Dihydroxyacetone (Organic) | 5.0 |
| Deionized Water | 1.0 |
| Sodium Metabisulfite | 0.1 |
| Phosphoric Acid (50% Aq. Soln) | 0.25 |

B. E.L. Self-action Tanning Mist (see formula above)

6.1.1 PROCEDURE FOR DEPTH & EVENNESS STUDIES

Twenty nine panelists participated in the study. Baseline color measurements were obtained from the right and left ventral forearms. The products were applied on the skin and allowed to absorb for 15 minutes. Color measurements were obtained after 24 hours.

Decrease in reflectance ($\Delta L^*$) and increase in red coloration ($\Delta a^*$) and yellow coloration ($\Delta b^*$) values were calculated as compared to baseline skin color. Total color change $\Delta E^*$ was calculated as follows:

$$\Delta E^* = \sqrt{(\Delta L^*)^2 + (\Delta a^*)^2 + (\Delta b^*)^2}$$

Twenty Scotch tape strippings were obtained from the tanned skin after 24 hours of product treatment. Color measurements of skin were obtained before and after stripping. The stripped tape from 15 panelists was placed on Market Zerolith paper in ten groups of two strips. Chromameter measurements of each pair of strippings were obtained and darkness (L* values) and yellow (b* values) were analyzed.

At the 24 hour time point, about 5–6 measurements of color were obtained within a 2 inch×2 inch tanned area of 20 panelists. The standard deviation within these replicates indicated the evenness of tanning. If the standard deviation was high, it was indicative of uneven, blotchy effect. A low standard deviation indicated even and smooth coloration. Statistical difference was evaluated via one-sample T-test using the Statgraphics Statistical package.

6.1.2 DEPTH OF TAN

Figure 1:
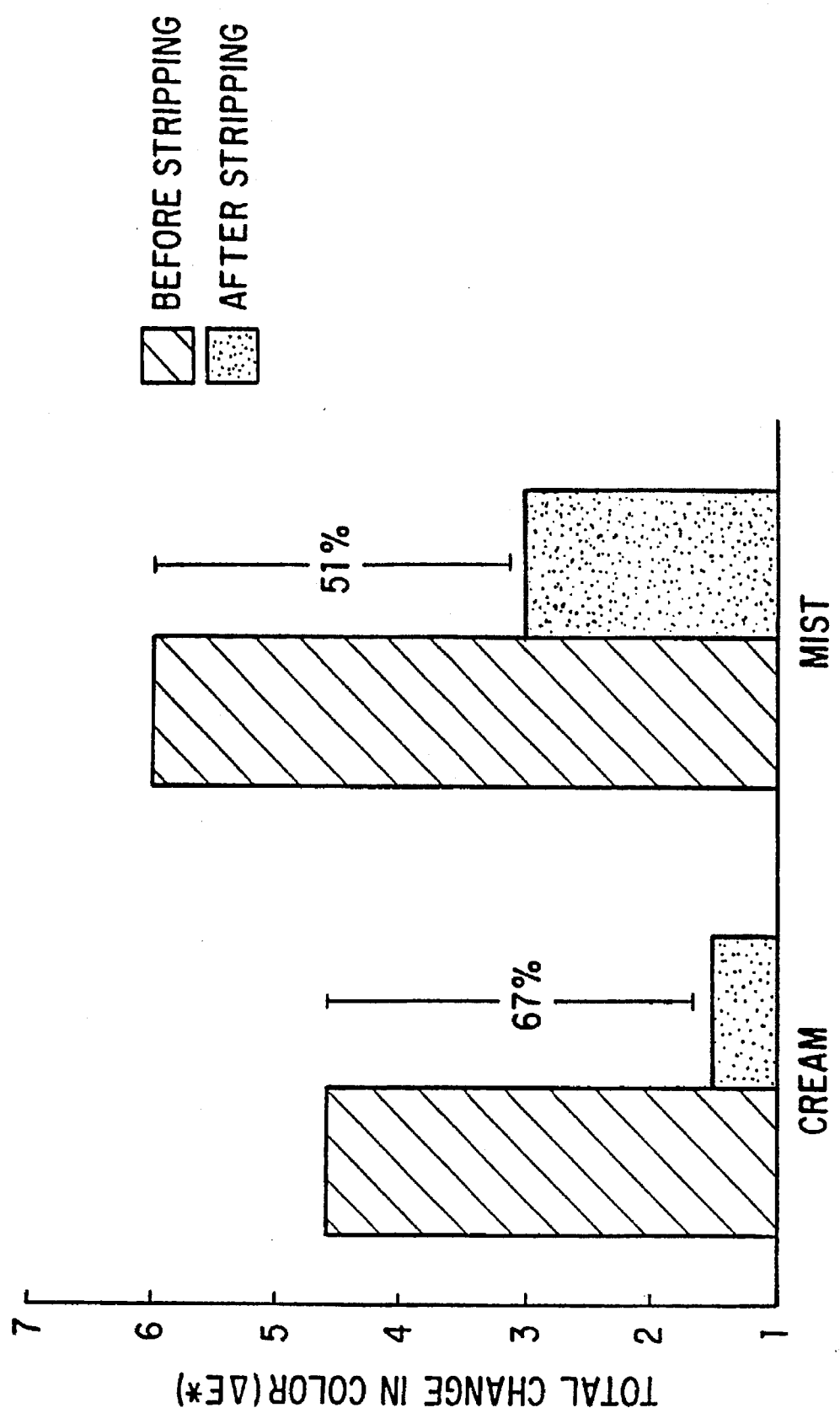
FIG. 1 is a bar graph illustrating the increased depth of the artificial tan achieved with a composition of the present invention, E.L. Selftan Mist, as compared to creams.

Most of the selftan coloration was removed after stripping with Scotch tape. The skin coloration with the Selftan Mist was deeper than the cream as observed from skin coloration after 20 Scotch Tape Strippings (Table 1 and FIG. 1). Percent reduction in color after stripping of skin treated with the E.L. Selftan cream was 67% while that of the Mist was 51%.

Figure 2:
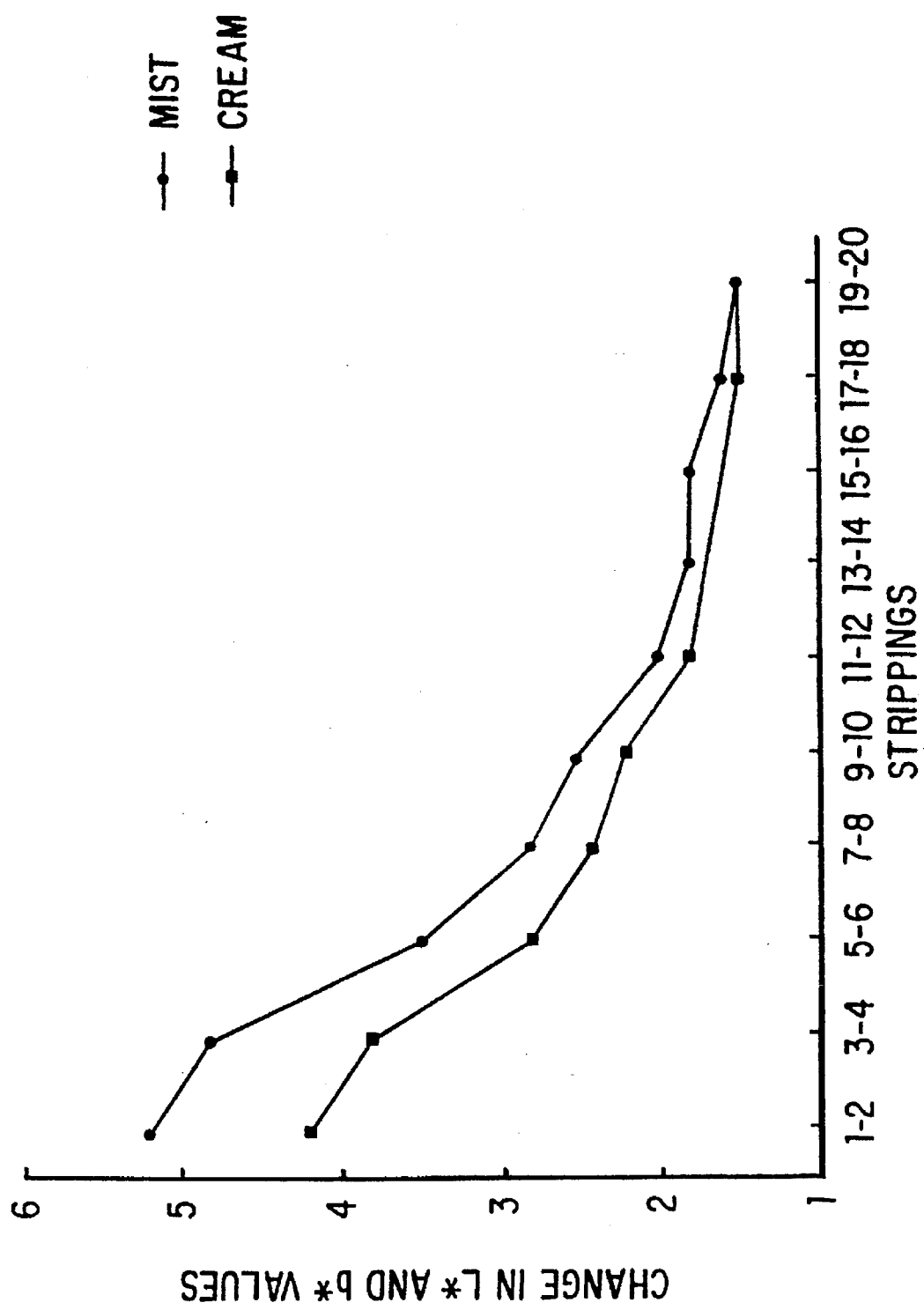
FIG. 2 is a graph illustrating the increased depth of the artificial tan achieved with the mist composition of the present invention as compared to creams. ΔL and Δb represent the decrease in reflectance and the increase in yellow coloration respectively.

The color of the scotch tape strippings (Table 2 and FIG. 2) indicated that most of the color was concentrated in the top ten layers of skin. Since there was more selftan on skin treated with the mist, more color came off the skin treated with the mist as compared to the cream.

TABLE 1

Depth of Self-action tanning With Selftan Cream and Mist
n = 29

|  | E.L. Selftan Cream | E.L. Selftan Mist |
| --- | --- | --- |
| Before Stripping |  |  |
| $\Delta L^*$ values | 2.57 | 3.73 |
| $\Delta a^*$ values | 1.40 | 1.93 |
| $\Delta b^*$ values | 3.57 | 4.30 |
| $\Delta E^*$ values | 4.61 | 6.01 |
| After Stripping |  |  |
| $\Delta L^*$ values | .24 | 1.15 |
| $\Delta a^*$ values | 1.31 | 2.03 |
| $\Delta b^*$ values | .73 | 1.76 |
| $\Delta E^*$ values | 1.52 | 2.92 |
| Percent Reduction | 67.10 | 51.38 |

TABLE 2

Depth of Self-action tanning With Selftan Cream and Mist
Total Change in Color ($\Delta L^*$ and $\Delta b^*$) (n = 15)

| Strippings | Mist | Cream |
| --- | --- | --- |
| 1–2 | 5.26 | 4.16 |
| 3–4 | 4.84 | 3.85 |
| 5–6 | 3.48 | 2.78 |
| 7–8 | 2.77 | 2.35 |
| 9–10 | 2.41 | 2.17 |
| 11–12 | 1.96 | 1.78 |
| 13–14 | 1.76 | 1.66 |
| 15–16 | 1.77 | 1.57 |
| 17–18 | 1.52 | 1.43 |
| 19–20 | 1.39 | 1.39 |

6.1.3 EVENNESS OF TAN

Figure 3:
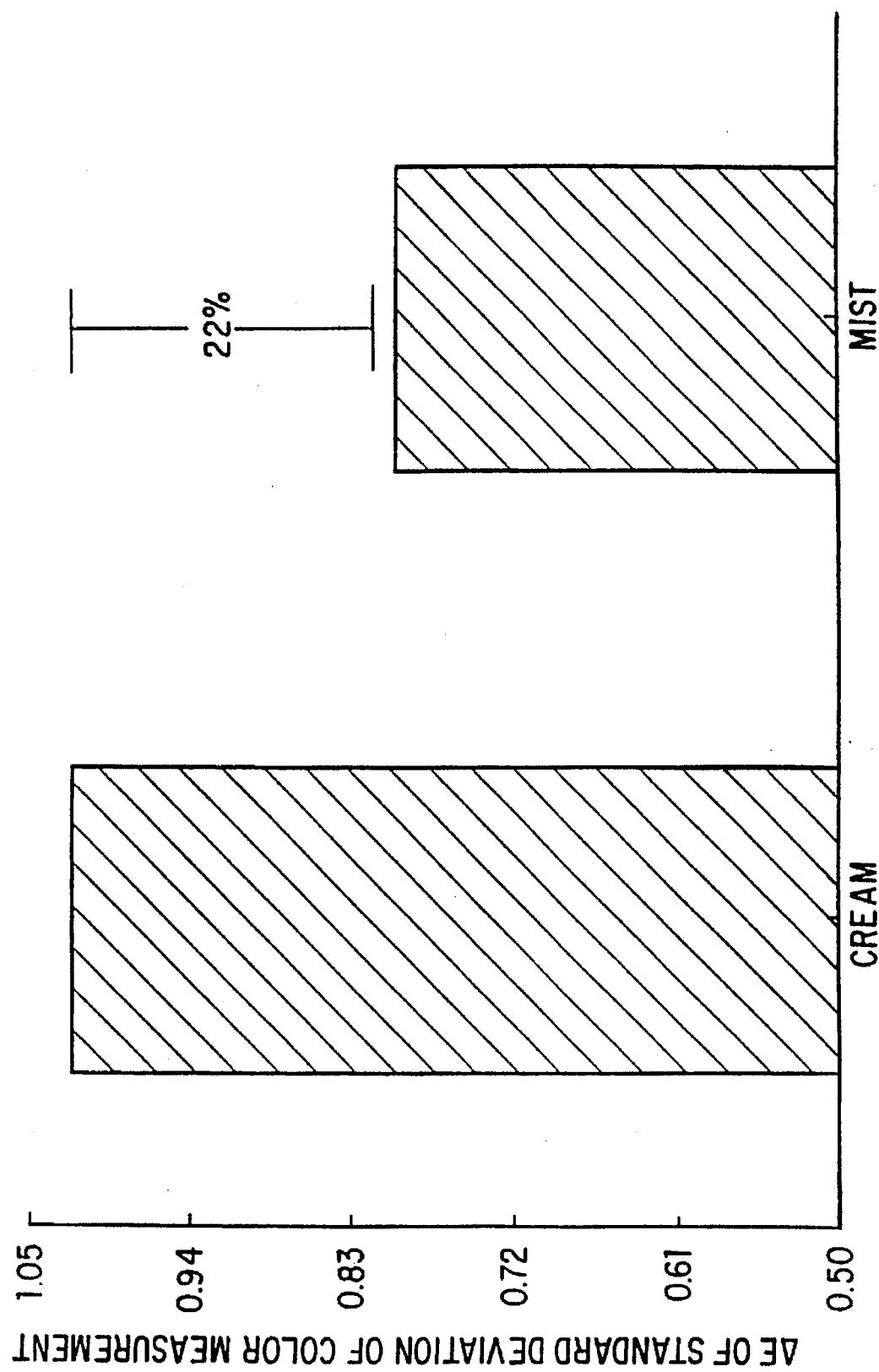
FIG. 3 is a bar graph illustrating the evenness of the artificial tan achieved with compositions of the present invention. A low standard deviation is indicative of evenness of color.

FIG. 3 shows that there was about 22% lower standard deviation with the Mist than the Cream. The difference is not highly significant (p=0.0247), however, the general trend indicated that the Selftan Mist caused an even tan possibly due to even distribution of DHA as it is released in the form of a spray.

6.2 EXAMPLE 2

SELF-ACTION TANNING WITH E.L. SELF ACTION TANNING CREAM AND MIST

This experiment was designed to compare the effect of E.L. Self-action Tanning Cream and Mist on increasing skin color. The results demonstrate that the onset of color was faster with the Selftan Mist than the Cream, also, it took a longer time for the color to fade with the Selftan Mist. The following products were tested:

E.L. Self-action Tanning Cream medium (see Example 1)

B. E.L. Self-action Tanning Mist (see formula above)

6.2.1 PROCEDURE FOR THE ONSET OF COLOR TEST

A total of twenty nine panelists participated in the study. Baseline color measurements were obtained from the right and left ventral forearms. The products were applied on the skin and allowed to absorb for 15 minutes. Color measurements were obtained after 2, 4, 5 hours and 24 hours and also after 3 and 5 days. Measurements were obtained from varying number of panelists at each time points, ranging from n=9 to n=29.

Decrease in reflectance and increase in red coloration and yellow coloration ($\Delta L^*$, $\Delta a^*$ and $\Delta b^*$ values) were calculated as compared to baseline skin color. Total color change $\Delta E^*$ was calculated as follows:

$$\Delta E^* = \sqrt{(\Delta L^*)^2 + (\Delta a^*)^2 + (\Delta b^*)^2}$$

There was a decrease in skin reflectance and an increase in skin redness and yellow coloration, due to the tanning effect of self-action tanning products. Total change in color shows that the onset of skin tanning was faster with the Tanning Mist than the cream.

Figure 4:
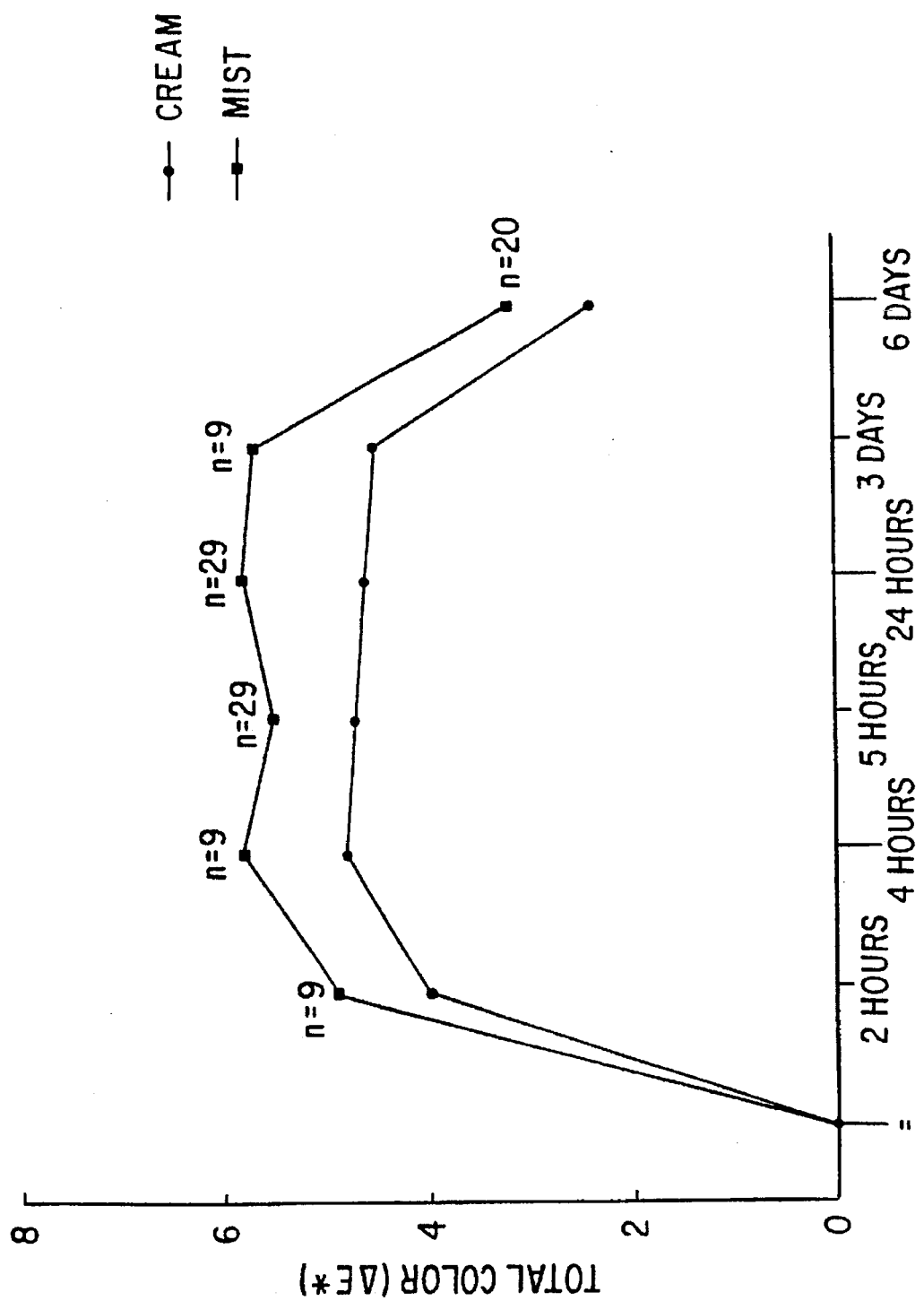
FIG. 4 is a graph illustrating the long lasting artificial tan effect of compositions of the present invention.

After 6 days most of the skin color faded, however as observed in Table 3 and FIG. 4, there was a slightly darker (35%) tan on skin treated with the Selftan Mist than the Cream. Thus it took a longer time for the color to fade with the Selftan Mist as compared to the Cream.

TABLE 3

Self Action Tanning With
E.L. Self Action Tanning Mist and Cream
Total change in Color $\Delta E^*$

|  |  | Cream | Mist |
|---|---|---|---|
| 2 Hours | (n = 9) | 4.08 | 4.91 |
| 4 Hours | (n = 9) | 4.89 | 5.94 |
| 5 Hours | (n = 29) | 4.73 | 5.55 |
| 24 Hours | (n = 29) | 4.61 | 6.01 |
| 3 days | (n = 9) | 4.48 | 5.96 |
| 6 days | (n = 20) | 2.24 | 3.42 |

6.3 EXAMPLE 3

LONG TERM IN-USE EFFECT OF SELF-ACTION TANNING MIST VS. CREAM

The following example demonstrates the improved tanning effects of Self-action Tanning Mist over the Self-action Tanning Cream. Self-action Tanning Mist was more effective than the cream in increasing skin color at each concentration tested. Further, this example demonstrates that a dose response was observed between the concentration of DHA and the total color increase.

6.3.1 PROCEDURE

A clinical study was designed to study the increase in skin color after long term use of self-action tanning cream and mist at different concentration. The following products were tested:
Group 1: 92-30 A1: Self Tan Cream PAR 3750/1, 5% DHA
92-30 A2: Self Tan Mist SN 1722/7, 5% DHA
Group 2: 92-30 B1: Self Tan Cream PAR 3750/2, 7.5% DHA
92-30 B2: Self Tan Mist AS 1969/3, 7.5% DHA
Group 3: 92-30 C1: Self Tan Cream PAR 3750/3, 10% DHA
92-30 C2: Self Tan Mist AS 1969/4, 10% DHA Seven to ten panelists were chosen for each group. The panelists were given a cream and a spray to be used on the right and left ventral forearms once every other day for 3 weeks. Color measurements were obtained at time 0 (baseline), 1 week and 3 weeks.

The panelists were instructed to apply the products all over the arms and spread the products with gloved hands to avoid staining of hands. They were instructed to allow the products to absorb for about 15 minutes before rolling down the sleeves to prevent staining of clothes and also to avoid streaking effect of the product.

Decrease in reflectance and increase in red coloration and yellow coloration ($\Delta L^*$, $\Delta a^*$ and $\Delta b^*$ values) were calculated as compared to baseline skin color. Total color change $\Delta E$, was calculated as follows:

$$\Delta E^* = \sqrt{(\Delta L^*)^2 + (\Delta a^*)^2 + (\Delta b^*)^2}$$

After 3 week use the color of the skin of some panelists using the 7.5% DHA and 10% DHA products was extremely dark but blotchy with dry patches. Some panelists actually exhibited a decrease in tanning effect after long term use possibly due to saturation.

Figure 5:
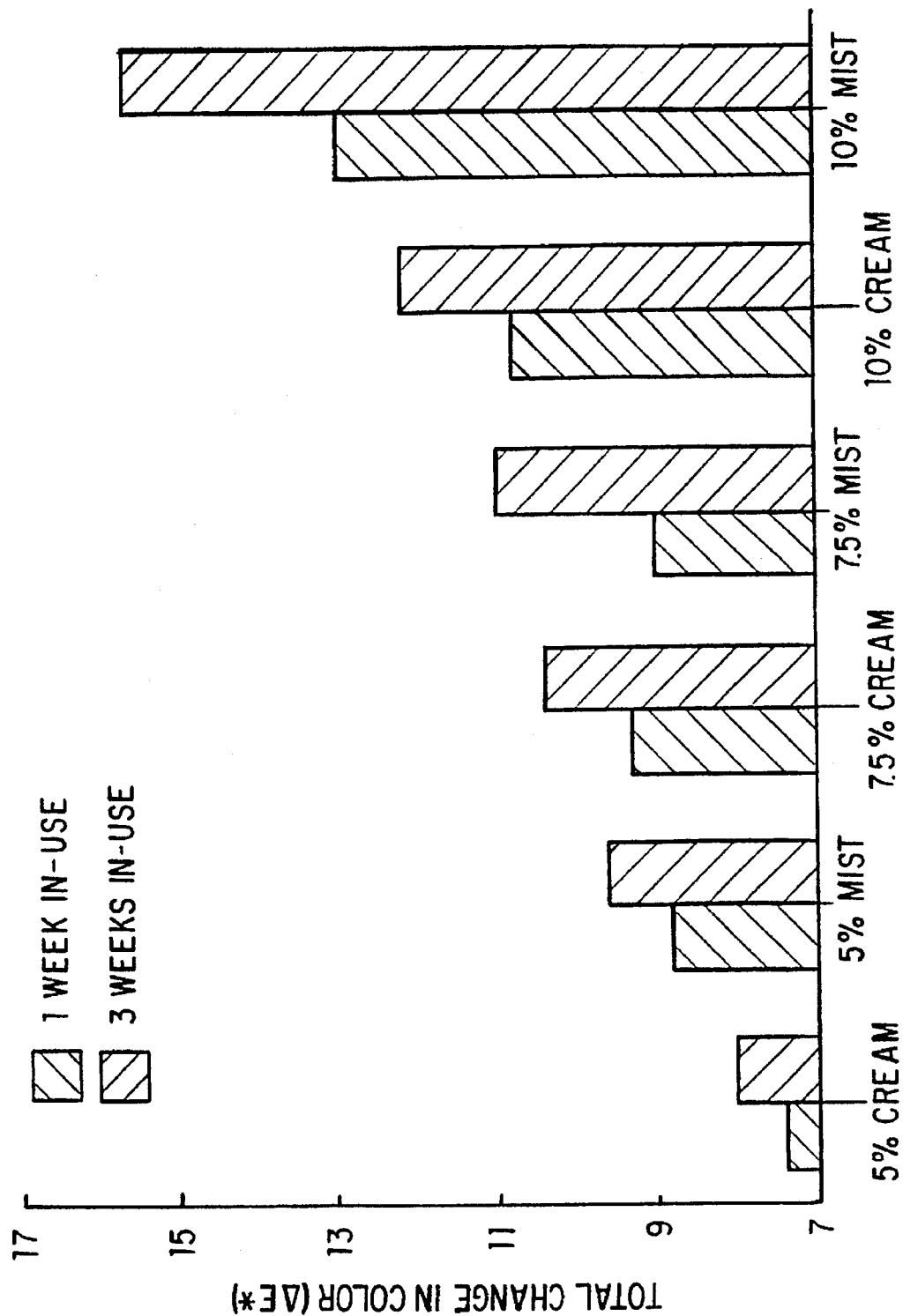
FIG. 5 is a bar graph illustrating the dose response of E.L. Selftan Mist at various concentrations over long term use (1 and 3 week in-use).

There was a decrease in skin reflectance and an increase in skin redness and yellow coloration, due to the tanning effect of self-action tanning products. Total change in color $\Delta E^*$ (FIG. 5) shows that the Self-action Tanning Mist was more effective than the cream in increasing skin color at each concentration tested.

A dose response was observed between the concentration of DHA and the total color increase (Table 4).

TABLE 4

Long Term In-Use Self-action Tanning Effect
of E.L. Selftan Mist versus E.L. Selftan Cream

|  | 5% DHA | | 7.5% DHA | | 10% DHA | |
|---|---|---|---|---|---|---|
|  | Cream | Mist | Cream | Mist | Cream | Mist |
| 1 week in-use $\Delta L^*$ values | 4.29 | 5.12 | 5.70 | 5.33 | 5.97 | 8.31 |
| $\Delta a^*$ values | 2.32 | 2.88 | 4.15 | 3.65 | 4.21 | 4.59 |
| $\Delta b^*$ values | 5.47 | 6.43 | 5.84 | 6.16 | 7.97 | 8.59 |
| $\Delta E^*$ values | 7.33 | 8.71 | 9.15 | 8.93 | 10.81 | 12.80 |
| 3 week in-use $\Delta L^*$ values | 5.26 | 5.84 | 6.28 | 6.90 | 7.40 | 10.37 |
| $\Delta a^*$ values | 2.8 | 3.13 | 4.56 | 4.33 | 4.67 | 5.67 |
| $\Delta b^*$ values | 5.68 | 6.84 | 6.90 | 7.60 | 8.64 | 9.52 |
| $\Delta E^*$ values | 8.23 | 9.52 | 10.38 | 11.14 | 12.30 | 15.18 |

6.4 EXAMPLE 4

SELF-ACTION TANNING WITH E.L. SELFTAN AND E.L. SELFTAN MIST COMPARISON WITH VARIOUS OTHER SELFTAN CREAMS

This experiment was designed to compare the self-action tanning effect of E.L. Self-action Tanning Mist as compared to various competing products. In particular, the example demonstrates that the tanning color achieved by the E.L. Selftan Mist closely resembles the color of a natural tan. The following products were tested:

1. E.L. Self-action Tanning Mist (see formula above)
2. E.L. Self-action Tanning Cream (medium) (see Example 1)
3. Coppertone Sunless Tanning Lotion (Schering-Plough)
4. Lancome Lait Auto-Bronzant Personnalise' 27 Medium Complexion Formula
5. Vaseline Intensive Care Moisturizing Sunless Tanning for Fair Skin (Chesebrough-Ponds)
6. Elizabeth Arden Spa for the Sun, Sunshine Selftanner for the Body 7. Elizabeth Arden Spa for the Sun, Sunshine Selftanner The Natural Look Selftanner for the Face SPF 15 (Dual tube)

6.4.1 PROCEDURE

A total of six panels (n=29 to n=7) were used in the study. Each panel was treated with the E.L. Mist on one arm and a Cream on the other arm. Treatment and panel distribution was as follows:

Group A: (n=29)
1. E.L. Self-action Tanning Mist
2. E.L. Self-action Tanning Cream (medium)

Group B: (n=10)
1. E.L. Self-action Tanning Mist
2. Coppertone

Group C: (n=10)
1. E.L. Self-action Tanning Mist
2. Vaseline Intensive Care

Group D: (n=10)
1. E.L. Self-action Tanning Mist
2. Elizabeth Arden

Group E: (n=8)
1. E.L. Self-action Tanning Mist
2. Lancome

Group F: (n=7)
1. E.L. Self-action Tanning Mist
2. Elizabeth Arden Natural Look Selftanner Baseline color measurements were obtained from the right and left ventral forearms. In-use amounts of the products were applied all over the arms and blended in. The panelists allowed the products to absorb for 15 minutes. Color measurements were obtained after 5 hours and 24 hours.

Decrease in reflectance and increase in red coloration and yellow coloration ($\Delta L^*$, $\Delta a^*$ and $\Delta b^*$ values) were calculated as compared to baseline skin color. Total color change $\Delta E^*$ was calculated as follows:

$$\Delta E^* = \sqrt{(\Delta L^*)2 + (\Delta a^*)2 + (\Delta b^*)2}$$

Natural Universe of Tanning was based on a panel of 19 volunteers exhibiting various degrees of sun tan. It was prepared as follows.

Skin tanning due to sun exposure was measured with a Chromameter. Increase in reflectance ($\Delta L^*$), red coloration ($\Delta a^*$) and yellow coloration ($\Delta b^*$) were calculated as compared to baseline skin color. Chroma or color change $\Delta C^*$ was calculated as follows:

$$Chroma \Delta C^* = \sqrt{(\Delta a^*)2 + (\Delta b^*)2}$$

The change in color Chroma values ($\Delta C^*$) and the change in skin darkness $\Delta L^*$ were plotted via cluster analysis from the Statgraphics statistical package. A cluster plane encompassing the distribution of normal skin tanning color values exhibited by the population was obtained. This represents the "Natural Universe of skin tanning" or a response region within which natural skin tan color was observed. The color change due to the self tanning response was plotted in the Natural Universe of tanning. The selftan response is "natural" if it is closer to the center of the Natural universe of tanning.

Difference between the $\Delta E^*$ values of the Mist and cream was analyzed via Wilcox test using the Statgraphics Statistical Package.

The panelists exhibited varying degrees of tanning with the E.L. Selftan Mist. In order to obtain one value for the Mist, the Darkness Chroma $\Delta C^*$ and total color values $\Delta E^*$ for the Mist were averaged and the corresponding Cream values normalized to the average Mist values. This technique allows for a reduction in the complexity of interpretation of data.

There was a decrease in skin reflectance and an increase in skin redness and yellow coloration, due to the tanning effect of self-action tanning products. Total change in color $\Delta E^*$ (FIG. 6) shows that the Self-action Tanning Mist was the most effective in increasing skin color as compared to all the creams tested. The Selftan Mist was significantly better (Z 0.05, 95% Confidence) than the Coppertone, Vaseline, Arden and EA Natural. The Lancome product and the Mist showed less difference (Table 5). These results are summarized as follows:

TABLE 5

Self-action Tanning With
E.L. Selftan Mist and Various Other Creams
Total Change in Color ($\Delta E^*$) 24 hours after treatment

|  | Cream | Mist | n | Significance Z value |
| --- | --- | --- | --- | --- |
| Group A: E.L. Selftan | 4.62 | 6.01 | 29 | 0.012 |
| Group B: Coppertone | 2.65 | 5.05 | 10 | 0.00728 |
| Group C: Vaseline | 2.21 | 7.30 | 10 | 0.00136 |
| Group D: Arden | 5.11 | 7.65 | 10 | 0.00171 |
| Group E: Lancome | 4.50 | 5.47 | 8 | 0.318 |
| Group F: EA Natural | 4.00 | 5.2 | 7 | 0.251 |

6.4.2 COMPARISON OF SELFTAN WITH NATURAL TAN

The change in color Chroma values ($\Delta C^*$) and the change in skin darkness ($\Delta L^*$) was plotted and overlapped with the natural skin tan cluster plane (FIGS. 7 and 8). It was observed that the Self-action skin tanning response of E.L. Mist, E.L. Cream and Arden Cream was within the Natural Universe of skin tanning; however, the Selftan Mist appeared to be closer to the center of the Color Universe than the Creams. Vaseline, Coppertone and also Lancome Selftan products were not within the Natural Universe of tanning. The Lancome product which appeared to be as effective as the Mist in terms of total color did not fall within the Natural universe of tanning since it increased the intensity of color values (red and yellow) more than the darkness, thereby giving more of a "stained" look than a "tanned" look. Skin color of selftan with Elizabeth Arden Natural Selftan product was similar to E.L. Self-action cream.

In order for the selftan to be closer to the center of the Universe, the color increase must be in proportion to the decrease in reflectance. A product might appear to darken the skin significantly as observed by total increase in color ($\Delta E^*$), however, observation of the Chroma ($\Delta C^*$) and Reflectance ($\Delta L^*$) reveals whether the darkened look was like a colored or "stained" look or closer to the natural tan of the skin.

TABLE 6

Self Action Tanning Response of E.L. Selftan Mist and Various Selftan Creams

| Product | Darkness ΔL* values | Chroma ΔC* values | Total color ΔE* values |
|---|---|---|---|
| 5 Hours | | | |
| E.L. Mist | 3.42 | 5.09 | 6.14 |
| Lancome | 2.32 | 3.92 | 4.55 |
| E.A. Natural | 2.74 | 4.13 | 4.77 |
| E.L. Cream | 2.68 | 4.12 | 4.88 |
| Arden | 2.32 | 3.29 | 4.02 |
| Coppertone | .96 | 2.86 | 3.16 |
| Vaseline | 1.09 | 3.21 | 3.45 |
| 24 Hours | | | |
| E.L. Mist | 3.85 | 4.99 | 6.30 |
| Lancome | 1.77 | 4.24 | 4.85 |
| E.A. Natural | 2.81 | 3.57 | 4.54 |
| E.L. Cream | 2.57 | 3.57 | 4.53 |
| Arden | 2.18 | 3.11 | 3.94 |
| Coppertone | 1.25 | 2.66 | 3.10 |
| Vaseline | .60 | 1.61 | 1.79 |

It is apparent that many modifications and variations of this invention as hereinabove set forth may be made without departing from the spirit and scope thereof. The specific embodiments described herein are given by way of example only and the invention is limited only the terms of the appended claims.

What is claimed is:

1. A sprayable cosmetic composition, for artificially tanning the skin wherein said composition is applied to the skin in an atomized droplet form, comprising from about 2.5 to about 10% by weight of dihydroxyactone and from about 5 to about 75% by weight of one or more penetration enhancers, in an aqueous base which is free of oil or alcohol.

2. A sprayable cosmetic composition, for artificially tanning the skin wherein said composition is applied to the skin in an atomized droplet form, which comprises:
   (a) from about 2.5% to about 10% by weight of dihydroxyacetone;
   (b) from about 25% to about 95% by weight of water; and
   (c) one or more penetration enhancers; said composition being free of alcohol and oil.

3. A sprayable cosmetic composition, for artificially tanning the skin wherein said composition is applied to the skin in an atomized droplet form, which comprises:
   (a) from about 2.5% to about 10% by weight of dihydroxyacetone;
   (b) from about 25% to about 95% by weight of water;
   (c) from about 5% to about 72.5% by weight of one or more penetration enhancers; said composition being free of alcohol and oil.

4. A cosmetic composition, sprayable in atomized droplet form, for artificially tanning the skin which comprises:

| | Approximate Weight Percent |
|---|---|
| Deionized Water | 63.0 |
| Dihydroxyacetone | 5.0 |
| 1,3 butylene glycol | 3.0 |
| UCON 50 HB 660 | 0.5 |
| Cropeptide W | 0.2 |
| Arasolve DMI | 10.0 |
| Protomate 600-ML | 1.5 |
| Euxyl K-400 | 0.2 |
| Transcutol | 10.0 |
| Dermol GL-7A | 5.0 |
| Surfactol 365 | 1.0 |

5. The cosmetic composition of claim 1, 2, or 3 wherein said penetration enhancer is dimethyl isosorbide, diethyl glycol monoethyl ether or a combination thereof.

6. The cosmetic composition of claim 1, 2, or 3 which is applied to the skin by a spray applicator.

7. The cosmetic composition of claim 1, 2 or 3 which is applied to the skin in an aerosol spray.

8. The cosmetic composition of claim 1, 2 or 3 which further comprises about 2% to about 8% by weight of a sunscreen agent selected from the group consisting of octyldimethyl PABA, benzophenone-4, DEA-methoxycinnanate, 2-phenyl-benzimidazole-5-sulphonic acid and TEA salicylate.

9. The cosmetic composition of claim 1, 2 or 3 wherein said composition dries more quickly than a cream or emulsion system.

10. A method of artificially tanning the skin which comprises applying an effective amount of a cosmetic preparation of claim 1, 2 or 3 wherein the artificial tan is more even, deeper and longer lasting than the artificial tan achieved by non-aqueous based compositions.

11. A method of artificially tanning the skin which comprises applying an effective amount of a quick drying cosmetic composition of claim 1, 2 or 3.

12. An improved method of artificially tanning the skin which comprises applying in an atomized droplet form an amount of a cosmetic composition according to claim 1, 2, 3 or 4.

13. The method of claim 10 or 11 wherein said composition is applied by a spray or aerosol application.

14. A method of artificially tanning the skin which comprises applying in an atomized droplet form an effective amount of a sprayable cosmetic preparation comprising from about 2.5 to about 10% by weight of dihydroxyacetone and from about 5 to about 75% by weight of one or more penetration enhancers in an aqueous base which is free of oil or alcohol.

* * * * *